(12) United States Patent
Kubo et al.

(10) Patent No.: US 8,415,399 B2
(45) Date of Patent: Apr. 9, 2013

(54) RETROVIRUS-INFECTION INHIBITOR

(75) Inventors: Yoshinao Kubo, Nagasaki (JP); Haruka Kamiyama, Nagasaki (JP)

(73) Assignees: Nagasaki University, Nagasaki (JP); Kowa Company, Ltd., Aichi (JP)

( * ) Notice: Subject to any disclaimer, the term of this patent is extended or adjusted under 35 U.S.C. 154(b) by 0 days.

(21) Appl. No.: 13/246,066

(22) Filed: Sep. 27, 2011

(65) Prior Publication Data

US 2012/0065263 A1 Mar. 15, 2012

Related U.S. Application Data

(62) Division of application No. 12/312,537, filed as application No. PCT/JP2007/068294 on Sep. 20, 2007.

(30) Foreign Application Priority Data

Nov. 17, 2006 (JP) .................................. 2006-312040

(51) Int. Cl.
*A01K 31/07* (2006.01)
*A61P 31/18* (2006.01)
*A61K 31/202* (2006.01)

(52) U.S. Cl.
USPC ................ 514/725; 514/560; 514/3.8; 435/4; 424/188.1

(58) Field of Classification Search .................. 514/725, 514/3.8; 435/4; 424/188.1
See application file for complete search history.

(56) References Cited

U.S. PATENT DOCUMENTS

| | | |
|---|---|---|
| 2003/0171339 A1 | 9/2003 | Sin et al. |
| 2004/0167215 A1 | 8/2004 | DeLuca et al. |

FOREIGN PATENT DOCUMENTS

| | | |
|---|---|---|
| JP | 1-275532 | 11/1989 |
| JP | 1-294660 | 11/1989 |
| JP | 7-258150 | 10/1995 |
| WO | 2005/072091 | 8/2005 |

OTHER PUBLICATIONS

Chandra et al. (FEBS letters, Aug. 1990, vol. 268 (2), pp. 415-421.*
International Search Report issued Dec. 11, 2007 in International (PCT) Application No. PCT/JP2007/068294.
H. Kamiyama et al., "Inhibition of HIV-1 infection by vitamin A analogue, geranylgeranoic acid (GGA)", The Japanese Society of Virology Gakujyutsu Shukai, p. 303, 1P146, 2002 & English translation.

(Continued)

*Primary Examiner* — Savitha Rao
(74) *Attorney, Agent, or Firm* — Wenderoth, Lind & Ponack, L.L.P.

(57) ABSTRACT

An infection inhibitor of retrovirus, particularly human immunodeficiency virus, comprising, as an active ingredient, at least one compound selected from the group consisting of a compound represented by the formula (I) (GGA) or a salt thereof, a compound represented by the formula (II) (NIK-333) or a salt thereof, and derivatives thereof.

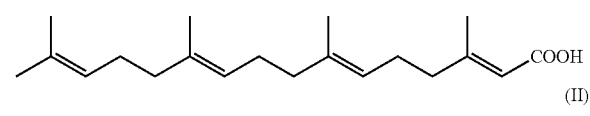
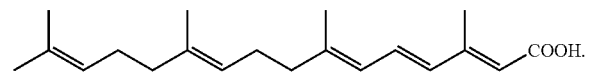

4 Claims, 12 Drawing Sheets

OTHER PUBLICATIONS

T. Okudaira et al., "NIK-333 inhibits growth of human T-cell leukemia virus type 1-infected T-cell lines and adult T-cell leukemia cells in association with blockade of nuclear factor-κB signal pathway", Molecular Cancer Therapeutics, vol. 5, No. 3, pp. 704-712, Mar. 2006.

A. F. B. Victoriano et al., "Inhibition of Human Immunodeficiency Virus Type 1 Replication in Latently Infected Cells by a Novel IκB Kinase Inhibitor", Antimicrobial Agents and Chemotherapy, vol. 50, No. 2, pp. 547-555, Feb. 2006.

H. Kamiyama et al., "Effect of acyclic retinoid in infection with human immunodeficiency virus type 1", vol. 81, No. 2, The Vitamin Society of Japan, p. 194, 2-IV-31, 2007, & English translation.

E. A. Berger et al., "A new classification for HIV-1", Nature, vol. 391, p. 240, Jan. 15, 1998.

C. M. Finnegan et al., "Ceramide, a target for antiretroviral therapy", Proc. Natl. Acad. Sci., USA vol. 101, No. 43, pp. 15452-15457, Oct. 26, 2004.

C. M. Finnegan et al., "Fenretinide inhibits HIV infection by promoting viral endocytosis", Antiviral Research, vol. 69, No. 2, pp. 116-123, Feb. 2006.

Y. Shidoji et al., "Natural occurrence of cancer-preventive geranylgeranoic acid in medicinal herbs", Journal of Lipid Research, vol. 45, No. 6, pp. 1092-1103, 2004.

Y. Muto et al., "Prevention of Second Primary Tumors by an Acyclic Retinoid in Patients with Hepatocellular Carcinoma", The New England Journal of Medicine, vol. 340, No. 13, p. 1046-1047, Apr. 1, 1999.

Y. Soda et al., "Establishment of a New System for Determination of Coreceptor Usages of HIV Based on the Human Glioma NP-2 Cell Line", Biochemical and Biophysical Research Communications, vol. 258, No. 2, pp. 313-321, May 10, 1999.

W. S. Pear et al., "Production of high-titer helper-free retroviruses by transient transfection", Proc. Natl. Acad. Sci., vol. 90, No. 18, pp. 8392-8396, Sep. 15, 1993.

Y. Yokomaku et al., "Impaired Processing and Presentation of Cytotoxic-T-Lymphocyte (CTL) Epitopes are Major Escape Mechanisms from CTL Immune Pressure in Human Immunodeficiency Virus Type 1 Infection", Journal of Virology, vol. 78, No. 3, pp. 1324-1332, Feb. 2004.

R. Tanaka et al., "Unique Monoclonal Antibody Recognizing the Third Extracellular Loop of CXCR4 Induces Lymphocyte Agglutination and Enhances Human Immunodeficiency Virus Type 1-Mediated Syncytium Formation of Productive Infection", Journal of Virology, vol. 75, No. 23, pp. 11534-11543, Dec. 2001.

Y. Maeda et al., "All-*trans* retinoic acid attacks reverse transcriptase resulting in inhibition of HIV-1 replication", Hematology, vol. 12, No. 3, pp. 263-266, Jun. 2007.

S. Mehta et al., "Effects of Vitamins, Including Vitamin A, on HIV/AIDS Patients", Vitamins and Hormones, Elsevier, Inc., vol. 75, Chapter 13, pp. 355-383, 2007.

Wiysonge CSU et al., Vitamin A supplementation for reducing the risk of mother-to-child transmission of HIV infection (Review), J. Wiley & Sons, Ltd., The Cochrane Library 2009, Issue 2, pp. 1-27.

Yoshida (Oncogene, vol. 24, 2005, pp. 593-5937).

* cited by examiner

GGA concentration

1:untreated (0μM), 2:5μM, 3:10μM, 4:20μM, 5:50μM fenretinide concentration

1:untreated (0μM), 2:0.2μM, 3:0.4μM, 4:1μM, 5:2μM

NIK-333 concentration

1:untreated (0μM)、 2:2μM、 3:5μM、 4:10μM、 5:20μM

RETROVIRUS-INFECTION INHIBITOR

This application is a Divisional of U.S. application Ser. No. 12/312,537, filed May 15, 2009, which is a national stage application of International application No. PCT/JP2007/068294, Filed Sep. 20, 2007.

TECHNICAL FIELD

The present invention relates to a retrovirus-infection inhibitor. More particularly, the present invention relates to an infection inhibitor of retrovirus such as human immunodeficiency virus and the like, comprising a certain retinoid analog as an active ingredient.

BACKGROUND ART

Retrovirus is a generic term of viruses belonging to Retroviridae, which have RNA as genome, and synthesize, in the primary step of self-replication, DNA using RNA as a template by the action of reverse transcriptase (RNA dependent DNA polymerase) they have. Retroviridae consists of three subfamilies (Oncovirinae, Lentivirinae, Spumavirinae). Retrovirus is known to infect and proliferate in various animals such as birds and mammals as hosts, and cause sarcoma, leukemia, cancer and the like. As retrovirus using human as a host, human T cell leukemia virus (HTLV), human immunodeficiency virus (HIV) and the like have been reported. HIV is known as a causative virus of acquired immunodeficiency syndrome (AIDS), a severe immunodeficiency.

AIDS has been suppressed to some extent by the development of compounds that inhibit reverse transcriptase and protease essential for HIV replication, and establishment of a combination therapy using such compounds. On the other hand, the emergence of resistant viruses is recognized as a major concern, and the development of a compound that inhibits a mechanism essential for HIV replication, which is other than reverse transcriptase and protease, has been desired.

HIV infects using, as a receptor, CD4 molecule presented on cellular membranes of helper T cell and macrophage. In this case, it requires an co-factor (coreceptor) that cooperates with CD4 molecule and promotes entry of the virus. As the coreceptor, chemokine (inflammatory cytokine) receptors CXCR4 and CCR5 have been identified at present (non-patent document 1).

As mentioned above, HIV recognizes CD4 and a series of chemokine receptors (e.g., CXCR4 and the like) of the target cell and enters the cell by fusion of viral envelope and cellular membrane. Therefore, a change in lipid, which is the constituent component of the membrane, is considered to affect HIV infection. Fenretinide (4-Hydroxyphenylretinoid), a retinoid analog, is known to specifically increase the ceramide level in the lipid component of membrane, and has already been reported to suppress intracellular entry of HIV (non-patent document 2, non-patent document 3). However, since fenretinide shows high cytotoxicity, its clinical application is difficult.

non-patent document 1: Berger, E. A., Doms, R. W., Fenyo, E.-M., Korber, B. T. M., Littman, D. R., Moore, J. P., Sattentau, Q. J., Schuitemaker, H., Sodroski, J., and Weiss, R. A. 1998. A new classification for HIV-1. Nature 391, 240.

non-patent document 2: Finnegan, C. M., Rawat, S. S., Puri, A., Wang, J. M., Ruscetti, F. W., and Blumenthal, R. 2004. Ceramide, a target for antiretroviral therapy. Proc. Natl. Acad. Sci. USA 101, 15452-15457.

non-patent document 3: Finnegan, C. M., and Blumenthal, R. 2006. Fenretinide inhibits HIV infection by promoting viral endocytosis. Antiviral Res. 69, 116-123.

non-patent document 4: Shidoji, Y., and Ogawa, H. 2004. Natural occurrence of cancer-preventive geranylgeranoic acid in medicinal herbs. J. Lipid Res. 45, 1092-1103.

non-patent document 5: Muto, Y., Moriwaki, H., and Saito, A. 1999. Prevention of second primary tumors by an acyclic retinoid in patients with hepatocellular carcinoma. N. Engl. J. Med. 340, 1046-1047.

DISCLOSURE OF THE INVENTION

Problems to be Solved by the Invention

The present invention aims to provide a retrovirus-infection inhibitor targeting intracellular entry of retrovirus such as HIV and the like.

Means of Solving the Problems

The present inventors have conducted intensive studies in view of the above-mentioned problems and found that acyclic retinoid different from fenretinide has an HIV infection suppressive action. In addition, they have confirmed that its cytotoxicity is remarkably reduced as compared to fenretinide, which resulted in the completion of the present invention.

Accordingly, the present invention provides the following.

[1] A retrovirus-infection inhibitor comprising, as an active ingredient, at least one compound selected from the group consisting of a compound represented by the formula (I) or a salt thereof, a compound represented by the formula (II) or a salt thereof, and derivatives thereof:

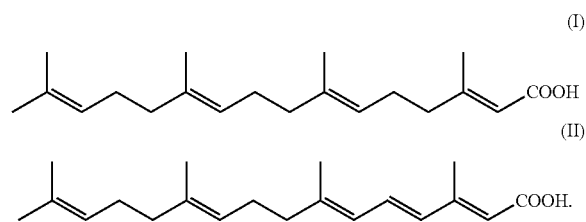

[2] The inhibitor of the above-mentioned [1], wherein the active ingredient is a compound represented by the formula (I) or a salt thereof, or a compound represented by the formula (II) or a salt thereof.

[3] The inhibitor of the above-mentioned [1] or [2], wherein the retrovirus is a human immunodeficiency virus.

[4] The inhibitor of any of the above-mentioned [1] to [3], wherein the inhibition of retrovirus infection is based on a CXCR4 expression lowering action.

[5] A therapeutic agent for HIV infection, comprising, as an active ingredient, at least one compound selected from the group consisting of a compound represented by the formula (I) or a salt thereof, a compound represented by the formula (II) or a salt thereof, and derivatives thereof.

[6] A method of suppressing retrovirus infection, comprising administering an effective amount of at least one compound selected from the group consisting of a compound represented by the formula (I) or a salt thereof, a compound represented by the formula (II) or a salt thereof, and derivatives thereof to a subject in need of the administration.

[7] The method of the above-mentioned [6], wherein a compound represented by the formula (I) or a salt thereof, or a compound represented by the formula (II) or a salt thereof is administered in an effective amount to the subject.

[8] The method of the above-mentioned [6] or [7], wherein the retrovirus is a human immunodeficiency virus.

[9] The method of any of the above-mentioned [6] to [8], wherein the suppression of retrovirus infection is based on a CXCR4 expression lowering action.

[10] A therapeutic method of HIV infection, comprising administering an effective amount of at least one compound selected from the group consisting of a compound represented by the formula (I) or a salt thereof, a compound represented by the formula (II) or a salt thereof, and derivatives thereof to a subject in need of the administration.

Effect of the Invention

The retrovirus-infection inhibitor provided by the present invention inhibits intracellular entry of retrovirus, particularly human immunodeficiency virus (HIV), and shows reduced cytotoxicity as compared to conventional ones.

BEST MODE FOR CARRYING OUT THE INVENTION

Figure 1:
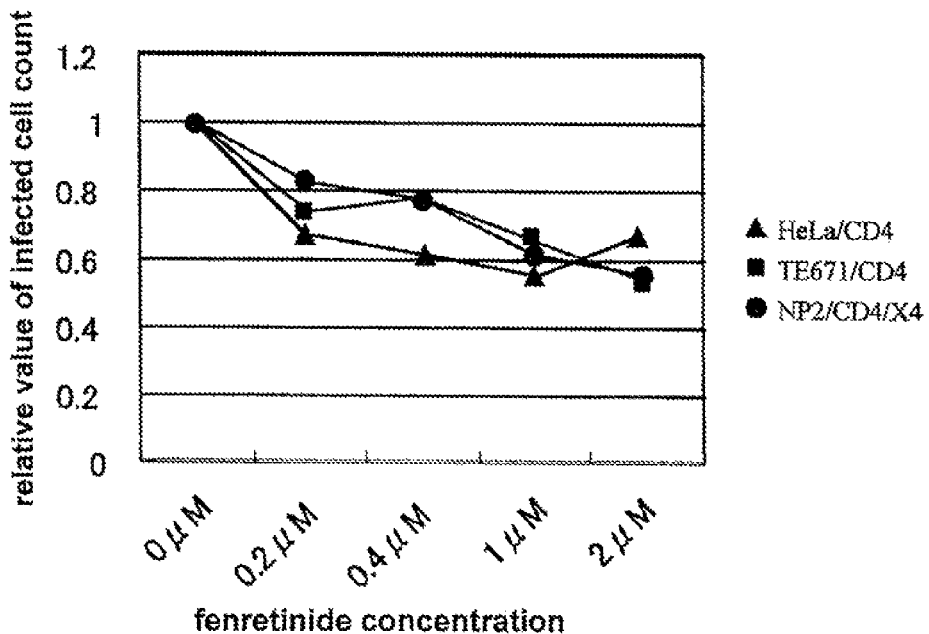
FIG. 1 is a graph showing an influence of fenretinide on HIV infection.

Unless otherwise specified, any technical or scientific term used in the present specification have the same meaning as that generally understood by those of ordinary skill in the art in the technical field to which the present invention belongs. Any methods and materials similar or equivalent to those described in the present specification can be used for practicing or testing the present invention. Preferable methods and materials are described in the following. All publications and patents referred to in the present specification are hereby incorporated by reference for the purpose of, for example, describing or disclosing constructed products and methodology described in publications, which are usable in connection with the described invention.

A compound represented by the formula (I) contained as an active ingredient in the present invention is known as geranylgeranoic acid (GGA) contained in herbs, which has been reported to be expected as a cancer therapeutic drug or cancer preventive drug since it increases the ceramide level of membrane lipid, and induces apoptosis in hepatoma cells (non-patent document 4). In the present specification, a compound represented by the formula (I) is sometimes abbreviated as GGA. GGA is a known compound, and can be synthesized according to a method reported previously, or according thereto.

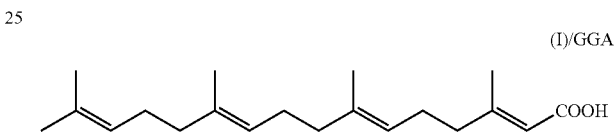

(I)/GGA

A compound represented by the formula (II) is a known compound also referred to as NIK-333, which is known to show an anticancer effect and a carcinogenesis preventive action (non-patent document 5). In the present specification, a compound represented by the formula (II) is also sometimes abbreviated as NIK-333.

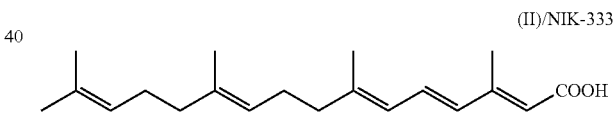

(II)/NIK-333

A compound represented by the formula (I) and a compound represented by the formula (II) to be contained in the infection inhibitor of the present invention as active ingredients may be derivatized as long as they have a retrovirus-infection suppressive action. Derivatization produces a compound more effective in terms of its specificity and effect, pharmacokinetics and the like. Derivatization can be performed by various methods and reactions generally performed in the pertinent field according to desired modifications. A compound represented by the formula (I) and a compound represented by the formula (II), as well as derivatives thereof are also collectively referred to as the compound of the present invention.

The compound of the present invention can be used in the form of a salt with a base or an acid addition salt such as a salt with an inorganic base (e.g., alkali metal salts such as sodium salt, potassium salt and the like, alkaline earth metal salts such as calcium salt, magnesium salt and the like, ammonium salt), a salt with an organic base (e.g., organic amine salts such as triethylamine salt, diisopropylethylamine salt, pyridine salt, picoline salt, ethanolamine salt, triethanolamine salt, dicyclohexylamine salt, N,N'-dibenzylethylenediamine salt and the like), inorganic acid addition salts (e.g., hydrochloride, hydrobromide, sulfate, phosphate etc.), organic carboxylic acid.sulfonic acid addition salts (e.g., formate, acetate, trifluoroacetate, maleate, tartrate, fumarate, methanesulfonate, benzenesulfonate, toluenesulfonate etc.), a salt with a basic or acidic amino acid (e.g., arginine, aspartic acid, glutamic acid etc.) and the like.

The compound of the present invention may be any of a solvate (e.g., hydrate etc.) and a non-solvate, both of which are encompassed in the compound of the present invention.

The compound of the present invention can also be used as a prodrug. Here, the prodrug is a compound which is converted to the compound of the present invention with a reaction due to an enzyme, gastric acid, and the like under the physiological conditions in the body, that is, a compound which is enzymatically converted to the compound of the present invention with oxidation, reduction, hydrolysis, and the like in the body. For example, the compound of the present invention wherein carboxyl group (COOH), hydroxyl group (OH), amino group ($NH_2$, also including amide), mercapto group (SH) and the like possibly present in a molecule have been modified.

The retrovirus to be the target of the infection inhibitor of the present invention includes viruses that uses RNA transcription for life support, such as human immunodeficiency virus (HIV) (e.g., human immunodeficiency virus 1 (HIV-1) and the like), human T cell leukemia virus (HTLV), hepatitis virus (HBV, HCV etc.) and the like. Preferable retroviruses to be the target are HIV and HTLV. The infection inhibitor of the present invention is particularly useful for HIV infections. HIV infections refer to pathology of HIV infection such as AIDS and symptomatic or non-symptomatic HIV infections (including AIDS-related syndrome: ARC).

The retrovirus-infection inhibitor, particularly, an HIV infection inhibitor, of the present invention can be used as a medicament for the treatment of various retrovirus infections such as HIV infections. The "treatment" includes a treatment aiming at improvement, mitigation or cure of symptoms. For example, a treatment of HIV infections include a treatment aiming at improvement, mitigation or cure of symptoms due to HIV infection, and a treatment aiming at prevention or delay of onset of AIDS. Specifically, it includes a treatment aiming at suppression of increase or decrease in CD4 positive lymphocyte count, suppression of increase or decrease in NK cell activity, prophylaxis, improvement, mitigation or cure of ARC, prophylaxis or delay of onset of AIDS, prophylaxis, improvement, mitigation or cure of opportunistic infection, and improvement, mitigation or cure of AIDS symptoms. The symptom of ARC includes lymph node swelling, anorexia, diarrhea, body weight decrease, fever, fatigue, rash, bronchial asthma and the like.

The infection inhibitor of the present invention can be administered to mammals such as human, monkey, bovine and cat, preferably human.

The infection inhibitor of the present invention can be used for any of oral administration and parenteral administration such as injection administration, intrarectal administration, nasal administration, transdermal administration, transmucosal membrane administration, sublingual administration and the like. The compound of the present invention can be administered in the form of a conventional pharmaceutical preparation obtained by admixing with a solid or liquid pharmaceutically acceptable nontoxic carrier suitable for an administration method such as oral administration, intrarectal administration, injection administration, nasal administration, transdermal administration, transmucosal membrane administration, sublingual administration and the like. As the amount of the compound of the present invention to be used for a pharmaceutical preparation in the case of oral administration, the daily dose is generally 0.001 g-0.1 g per 1 kg body weight, as an effective amount of the compound of the present invention. In the case of parenteral administration, the daily dose is generally 0.0001 g-0.01 g per 1 kg body weight, as an effective amount of the compound of the present invention. The amount of the compound to be actually administered is determined according to the selection of compound, various dosage forms, age, body weight, sex of patients, disease condition, administration route and the like, and can be changed as appropriate. The retrovirus-infection inhibitor, particularly HIV-infection inhibitor, of the present invention has low toxicity and causes less side effects.

The dosage form of the infection inhibitor of the present invention includes, for example, oral agents (e.g., tablet, pill, powder, granule, capsule, troche, syrup etc.), injection, suppository, collunarium, preparation for transdermal administration (e.g., ointment, cream, adhesive preparation etc.), preparation for transmucosal membrane administration, hypoglottis, spray, inhalant and the like.

Examples of the pharmaceutically acceptable carrier include excipients such as lactose, cornstarch, sucrose, glucose, sorbitol, mannitol, maltose, trehalose, crystalline cellulose, carboxymethylcellulose, calcium carboxymethylcellulose, sodium hydrogen carbonate, dextrin and the like; binders such as methylcellulose, gum arabic, tragacanth, gelatin, hydroxypropylcellulose, hydroxypropylmethylcellulose, polyvinylpyrrolidone, pullulan, sucrose fatty acid ester and the like; thickeners such as sodium carboxymethylcellulose, calcium carboxymethylcellulose, polyvinylpyrrolidone, hydroxypropylcellulose, hydroxypropylmethylcellulose, methylcellulose and the like; lubricants such as magnesium stearate, calcium stearate, talc, light anhydrous silicic acid and the like; suppository base such as polyethylene glycol, cacao butter and the like; inorganic or organic solvents such as distilled water, distilled water for injection, sterile purified water, saline, vegetable oil (olive oil, sesame oil, soybean oil, corn oil, peanut oil), glycerol, ethanol, propylene glycol and the like; and the like. In addition, the pharmaceutical preparation of the present invention may contain additives such as preservatives (e.g., sodium benzoate, benzalkonium chloride, benzethonium chloride, methyl p-hydroxybenzoate, ethyl p-hydroxybenzoate, propyl p-hydroxybenzoate, butyl p-hydroxybenzoate, sorbic acid, potassium sorbate and the like); emulsifiers (e.g., glycerol monostearate and the like); pH adjusters containing buffer (e.g., hydrochloric acid, citric acid, acetic acid, tartaric acid, sodium hydrogen carbonate, sodium hydroxide, sodium carbonate and the like); and the like.

Moreover, it is also possible to use the infection inhibitor of the present invention and other medicament in combination. That is, the inhibitor can be used in combination with a therapeutic drug for opportunistic infection occurring in association with AIDS, other kind of anti-HIV agent, a medicament that improves immune function and the like. Specifically, antivirus agent, antibiotic, immune enhancer and the like can be mentioned.

Preferable examples of the antivirus agent that can be used in combination with the infection inhibitor of the present invention include nucleoside derivatives such as AZT (reverse transcriptase inhibitor), dideoxyinosine (ddI), dideoxycytidine (ddC), dideoxyadenosine (ddA), lamivudine (3TC), stavudine (d4T) and the like, protease inhibitors such as indinavir (IDV), saquinavir, ritonavir (RTV), nelfinavir and the like, interferons such as interferon α, interferon β, interferon γ and the like. One or more kinds of such antivirus agents and the HIV-infection inhibitor of the present invention can be used in combination.

Examples of the antibiotic that can be used in combination with the infection inhibitor of the present invention include antibacterial agent, antifungal agent (including antifungal agents for *Candida, carinii pneumonia* and the like) and the like. Preferable examples of the antibacterial agent include penicillin antibiotic, cephem antibiotic, macrolide antibiotic, tetracycline antibiotic, fosfomycin antibiotic, aminoglycoside antibiotic, newquinolone antibacterial agent and the like. Preferable examples of the antifungal agent include polyene antifungal agents, imidazole antifungal agents, triazole antifungal agents, allylamine antifungal agents, flucytosine (5-FC) antifungal agents and the like. Two or more kinds of such antibacterial agents and antifungal agents can be used as a combination agent.

Examples of the immunity enhancer that can be used in combination with the infection inhibitor of the present invention include medicaments considered to have an immunity enhancing action by T lymphocyte stimulation and the like. Specifically, neurotropin, glycyrrhizin, lentinan, isoprinosine and the like can be mentioned.

Moreover, various medicaments used for a symptomatic therapy of various symptoms of diseases caused by retrovirus infection, for example, HIV infection, can also be used in combination with the infection inhibitor of the present invention.

The medicaments to be used in combination with the infection inhibitor of the present invention can be administered simultaneously with the infection inhibitor of the present invention, or can be administered separately. The dose is an amount necessary for achieving an expected effect, which can be determined based on the information that should have already been reported for each medicament.

Moreover, the present invention provides a method of suppressing retrovirus infection, particularly HIV infection. Such method enables treatment of various retrovirus infections such as HIV infections.

EXAMPLES

The present invention is explained in more detail in the following by referring to Examples, which are not to be construed as limitative. In addition, the reagents, apparatuses and materials to be used in the present invention are commercially available unless otherwise specified.

Example 1

HIV Infection Suppressive Action and Cell Proliferation Suppressive Action-1

Method
(1) Reagent

Fenretinide (BIOMOL Research Laboratories Inc.), GGA (supplied by Dr. Shidouji of Siebold University of Nagasaki) and NIK-333 (Kowa Pharmaceutical Co., Ltd.) were each dissolved in ethanol to 5 mM, 5 mM and 50 mM to give stock solutions. The stock solutions were divided into small portions each for one time use and preserved at −20° C. until use.
(2) Cells NP2 is a cell line derived from human glioma, TE671 is a cell line derived from human rhabdomyosarcoma, and HeLa is a cell line derived from human uterine cervix cancer. Human NP2 cell and NP2 cell (NP2/CD4/X4 cell) that expresses CD4 and CXCR4, which are infection receptors of HIV, were supplied by Dr. Hoshino of Gunma University (Soda, Y., Shimizu, N., Jinno, A., Liu, H. Y., Kanbe, K., Kitamura, T., and Hoshino, H. 1999. Establishment of a new system for determination of coreceptor usages of HIV based on the human glioma NP-2 cell line. Biochem. Biophys. Res. Commun. 258, 313-321). Human TE671 cell (TE671/CD4 cell) and HeLa cell (HeLa/CD4 cell) that express CD4 were prepared by infecting TE671 cell (supplied by Dr. Amanuma of RIKEN) or HeLa cell (supplied by Dr. Sato of National Institute of Infectious Diseases) with mouse leukemia virus vector having CD4. Namely, the following were performed. CD4 gene was inserted into mouse leukemia virus vector plasmid pMX-puro (shared by Dr. Kitamura of University of Tokyo) and its plasmid DNA was named as CD4-puro. Three kinds of plasmids of the obtained CD4-puro plasmid, mouse leukemia virus gag-pol expression plasmid pGP (purchased from Takara) and pLPNSVG (purchased from Invitrogen) were transfected to 293T cells, and the culture supernatant thereof was inoculated to TE671 cell and HeLa cell. The cells survived by selection with puromycin were named as TE671/CD4 cell and HeLa/CD4 cell, respectively. Human 293T cells (Pear, W. S., Nolan, G. P., Scott, M. L., and Baltimore, D. 1993. Production of high-titer helper-free retroviruses by transient transfection. Proc. Natl. Acad. Sci. USA 90, 8392-8396), NP2/CD4/X4 cell, TE671/CD4 cell, HeLa/CD4 cell and 293T cells were cultured in Dulbecco-modified Eagle medium (Sigma Ltd. or Wako) containing 8% fetal bovine serum and antibiotic at 37° C. in the presence of 5% $CO_2$.

(3) Preparation of Plasmid DNA:

Plasmid DNAs (pLP1, pLP2) that express HIV gene necessary for preparation of HIV vector except env gene were purchased from Invitrogen. The plasmid DNA that expresses env gene of CXCR4-tropic HIV-1 (HXB2) and the plasmid DNA that expresses env gene of CCR5-tropic HIV-1 (JRFL) were both supplied by Dr. Yokomaku of Nagoya Medical Center (Yokomaku, Y., Miura, H., Tomiyama, H., Kawana-Tachikawa, A., Takiguchi, M., Kojima, A., Nagai, Y., Iwamoto, A., Matsuda, Z., and Ariyoshi, K. 2004. Impaired processing and presentation of cytotoxic-T-lymphocyte (CTL) epitopes are major escape mechanisms from CTL immune pressure in human immunodeficiency virus type 1 infection. J. Virol. 78, 1324-1332). The plasmid DNA (pLenti6/V5-GW/lacZ) that expresses HIV vector genome having LacZ as a marker gene was purchased from Invitrogen. These plasmid DNAs were introduced into competent *Escherichia coli* (Takara), and cultured in the presence of ampicillin. The plasmid DNA was purified from *Escherichia coli* grown in this way (Viogene).

(4) Preparation of CXCR4-Tropic HIV Vector pLP1; pLP2, pLenti6/V5-GW/LacZ and HXB2 env plasmid DNA (each 3 μg) were transfected to 293T cells, cultured in a 10 cm culture dish, according to a lipofection method (Mirus or Invitrogen). After 24 hr, the medium was exchanged with a fresh medium. The cells were culture for 24 hr more, and the culture medium was used for inoculation to target cells (NP2/CD4/X4 cell, TE671/CD4 cell, HeLa/CD4 cell). CXCR4-tropic HIV vector was present in the culture medium.

(5) Measurement of Infectivity Titer of HIV Vector

HIV vector was inoculated and the cells were cultured for 24 hr. The medium was exchanged with a fresh medium and the cells were further cultured for 24 hr. The cells were fixed with glutaraldehyde and stained with X-Gal overnight. The cells stained blue was counted and the value was used as an infectivity titer.

(6) Cytotoxicity Test

The cells were counted to observe the effect on cell proliferation.

Results (1) Suppression of HIV Infection and Cell Proliferation by Fenretinide

Fenretinide has already been reported to suppress HIV vector infection (Finnegan, C. M., Rawat, S. S., Puri, A., Wang, J. M., Ruscetti, F. W., and Blumenthal, R. 2004. Ceramide, a target for antiretroviral therapy. Proc. Natl. Acad. Sci. USA 101, 15452-15457; Finnegan, C. M., and Blumenthal, R. 2006. Fenretinide inhibits HIV infection by promoting viral endocytosis. Antiviral Res. 69, 116-123). Whether fenretinide also suppresses HIV vector infection as previously reported was confirmed in the present experimental system.

Fenretinide was added to Dulbecco-modified Eagle medium (Sigma Ltd. or Wako) containing 2% fetal bovine serum and antibiotic to various concentrations, and the target cells were cultured for 2 days at 37° C. in the presence of 5% $CO_2$. HIV vector (culture supernatant containing HIV vector, mentioned above) was inoculated to the cells and the infectivity titer was measured.

Separately, TE671/CD4 cell, NP2/CD4/X4 cell and HeLa/CD4 cell were counted to quantitatively analyze the influence of fenretinide on cell proliferation. Each cell was treated with each compound in the same manner as in the measurement of infectivity titer and cultured for 2 days.

Figure 2:
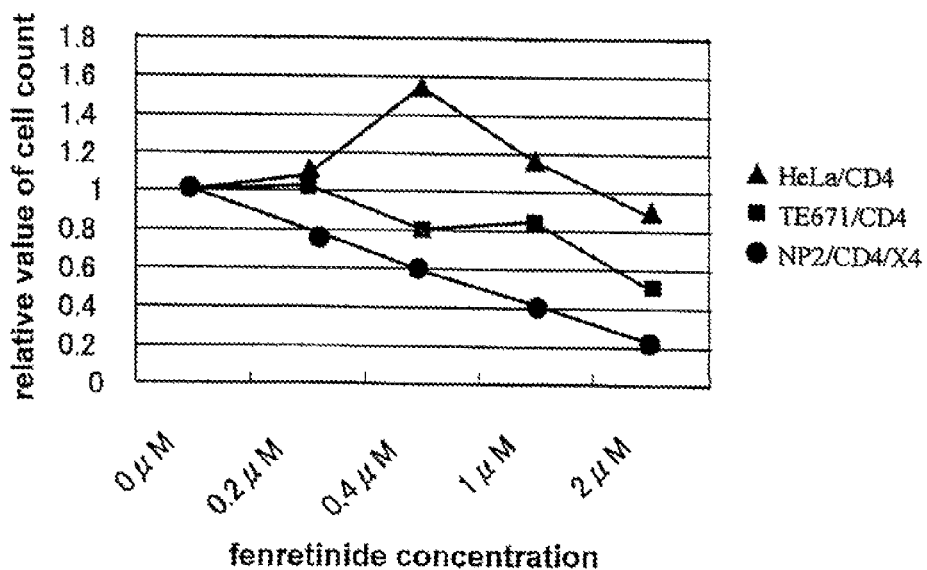
FIG. 2 is a graph showing an influence of fenretinide on cell proliferation.
Figure 4:
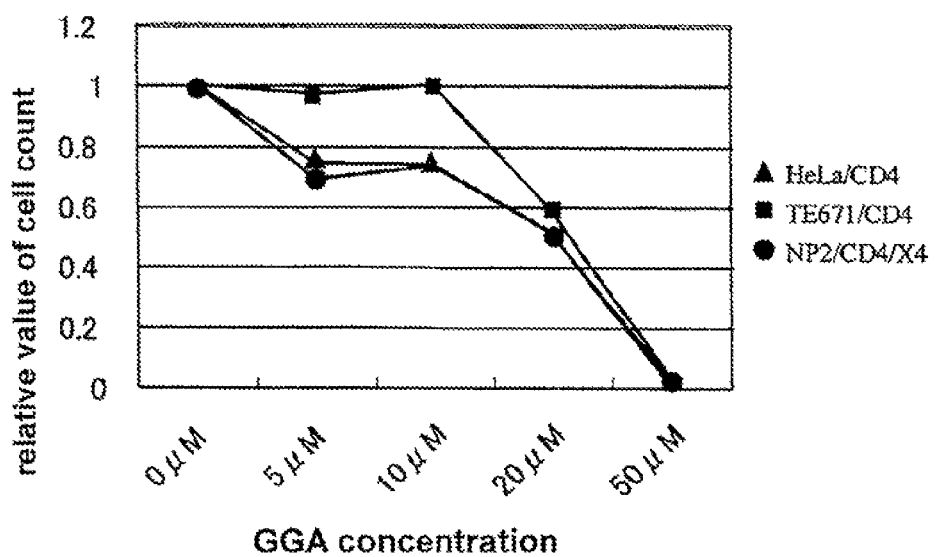
FIG. 4 is a graph showing an influence of GGA on cell proliferation.

The results of the infectivity titer measurement are shown in FIG. 1, and the results of the cell proliferation measurement are shown in FIG. 2. The measurement results are shown in relative values based on the value without fenretinide (0 µM) as 1. As shown in FIG. 1, fenretinide suppressed infectious property of HIV vector in a concentration-dependent manner. As shown in FIG. 2, however, it showed cytotoxicity on NP2/CD4/X4 cell and TE671/CD4 cell. The concentration necessary for suppressing HIV vector infection in each cell by 50% and the concentration necessary for suppressing cell proliferation by 50%, as calculated from those results, are shown in Table 1.

vector infection in a concentration-dependent manner. GGA showed a lower effect of suppressing HIV vector infection than fenretinide. However, cytotoxicity by GGA was lower than fenretinide in all the cells examined (FIG. 4).

The concentration of GGA necessary for suppressing HIV vector infection in each cell by 50% and the concentration of GGA necessary for suppressing cell proliferation by 50% are shown in Table 1 (above).

As shown in Table 1, GGA showed the same level of HIV vector infection suppressive effect and cell proliferation suppressive effect in each cell.

(3) Suppression of HIV Infection and Cell Proliferation by NIK-333

Figure 5:
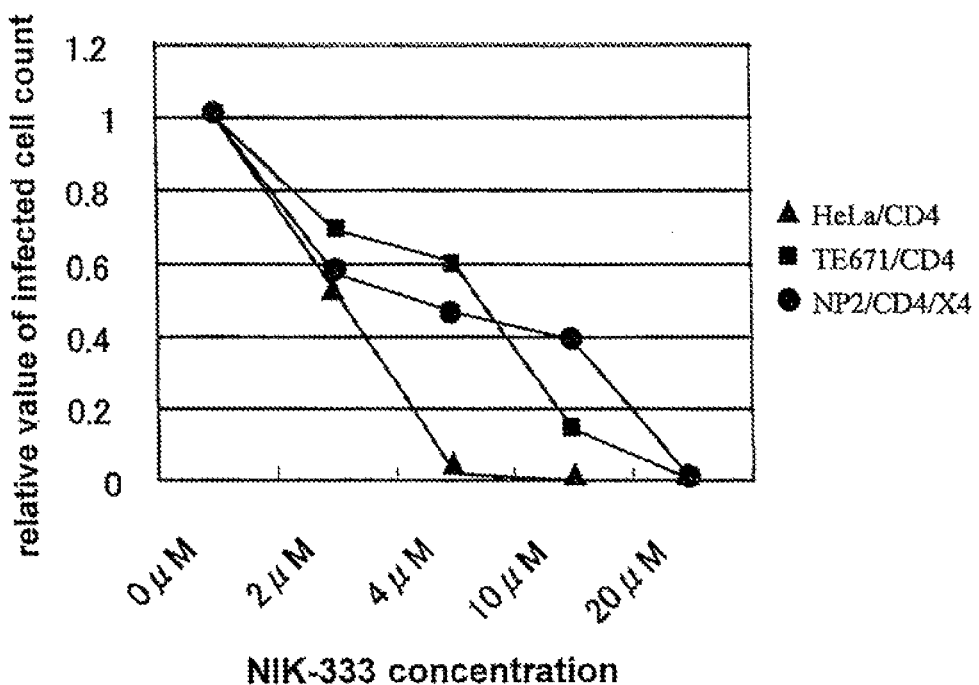
FIG. 5 is a graph showing an influence of NIK-333 on HIV infection.
Figure 6:
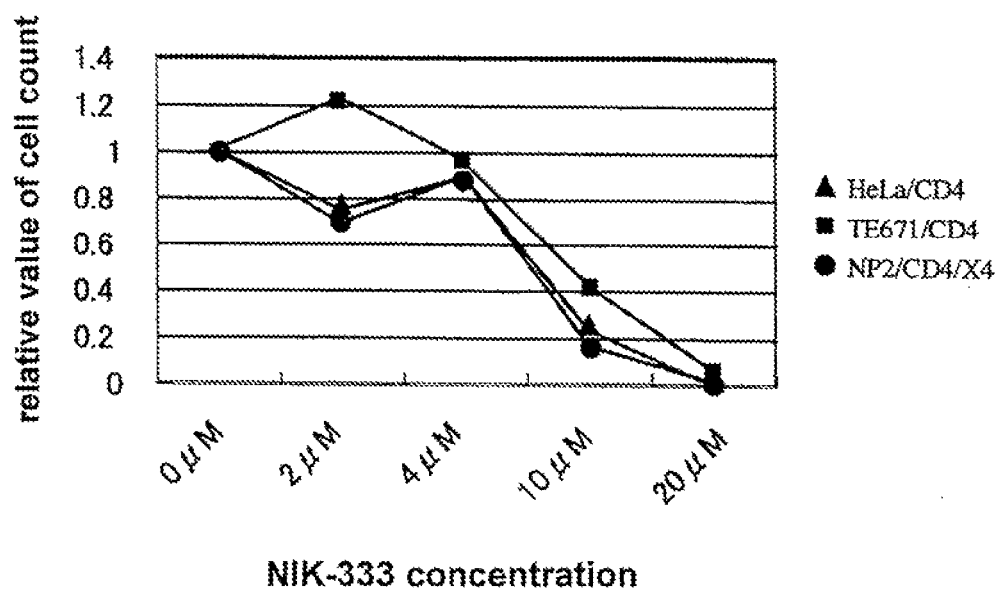
FIG. 6 is a graph showing an influence of NIK-333 on cell proliferation.

In the same manner as in fenretinide and GGA, the target cells were treated with NIK-333 and HIV vector was inoculated. The results of the infectivity titer measurement are shown in FIG. 5 and the results of the cell proliferation measurement are shown in FIG. 6. The measurement results are shown in relative values based on the value without NIK-333 (0 µM) as 1. The concentration of NIK-333 necessary for suppressing HIV vector infection in each cell by 50% and the concentration of NIK-333 necessary for suppressing cell proliferation by 50% are shown in Table 1 (above).

From the results of FIG. 5 and FIG. 6, NIK-333 is also shown to have an HIV vector infection suppressive action and a cell proliferation suppressive action. Furthermore, as shown in Table 1, different from fenretinide and GGA, NIK-333 showed a stronger HIV vector infection suppressive effect than a cell proliferation suppressive effect in any cell.

Example 2

Influence on HIV Infection Receptor Expression

Method

Fenretinide and GGA were added to Dulbecco-modified Eagle medium (Sigma Ltd. or Wako) containing 2% fetal bovine serum and antibiotic, to 2 µM and 20 µM, respectively. The target cells (HeLa/CD4 cell or NP2/CD4/X4 cell) were

TABLE 1

| | HeLa/CD4 cell | | TE671/CD4 cell | | NP2/CD4/X4 cell | |
|---|---|---|---|---|---|---|
| compound | concentration to suppress cell proliferation by 50% | concentration to suppress HIV infection by 50% | concentration to suppress cell proliferation by 50% | concentration to suppress HIV infection by 50% | concentration to suppress cell proliferation by 50% | concentration to suppress HIV infection by 50% |
| fenretinide | 2 µM or above | 2 µM | 2 µM | 2 µM | 0.7 µM | 2 µM |
| GGA | 20 µM | 20 µM | 25 µM | 25 µM | 20 µM | 20 µM |
| NIK-333 | 7 µM | 2 µM | 8 µM | 5 µM | 7 µM | 4 µM |

In HeLa/CD4 cell, fenretinide showed a stronger HIV vector infection suppressive effect than a cell proliferation suppressive effect. The effect was almost the same in TE671/CD4 cell, and the cell proliferation suppressive effect was stronger in NP2/CD4/X4 cell.

(2) Suppression of HIV Infection and Cell Proliferation by GGA

Figure 3:
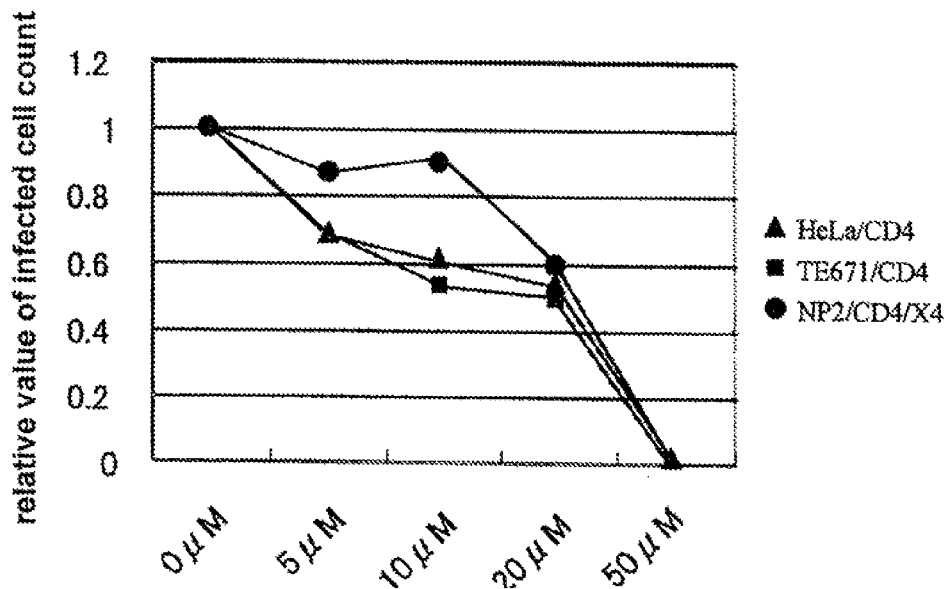
FIG. 3 is a graph showing an influence of GGA on HIV infection.

In the same manner as with fenretinide, the target cells were treated with GGA and HIV vector was inoculated. The results of the infectivity titer measurement are shown in FIG. 3, and the results of the cell proliferation measurement are shown in FIG. 4. The measurement results are shown in relative is values based on the value without GGA (0 µM) as 1. As shown in FIG. 3, GGA was found to suppress HIV cultured in the medium for 2 days at 37° C. in the presence of 5% $CO_2$. HeLa/CD4 cell and NP2/CD4/X4 cell were similar to those used in Example 1. The cells were treated with fenretinide or GGA and stained with anti-CD4 antibody conjugated with FITC (Sigma Ltd.). As a control, cells treated in the same manner except antibody was not used (Ab(−)) and cells treated in the same manner except the treatment with fenretinide or GGA was not performed (Ab(+)) were also examined. The fluorescence intensity of each cell was measured by a cytometer (Coulter) and evaluated as a cell surface expression amount of CD4. In the same manner, the cell treated with fenretinide or GGA was stained with rat anti-CXCR4 antibody (Tanaka, R., Yoshida, A., Murakami, T., Baba, E., Lichtenfeld, J., Omori, T., Kimura, T., Tsurutani, N., Fujii, N., Wang, Z.-X., Peiper, S. C., Yamamoto, N., and Tanaka, Y. 2001. Unique monoclonal antibody recognizing the third extracellular loop of CXCR4 induces lymphocyte agglutination and enhances human immunodeficiency virus type 1-mediated syncytium formation and productive infection. J. Virol. 75, 11534-11543), and then with rat anti-IgG antibody conjugated with FITC (Sigma Ltd.). The fluorescence intensity of each cell was measured by a cytometer (Coulter) and evaluated as a cell surface expression amount of CXCR4.

Results

Figure 7:
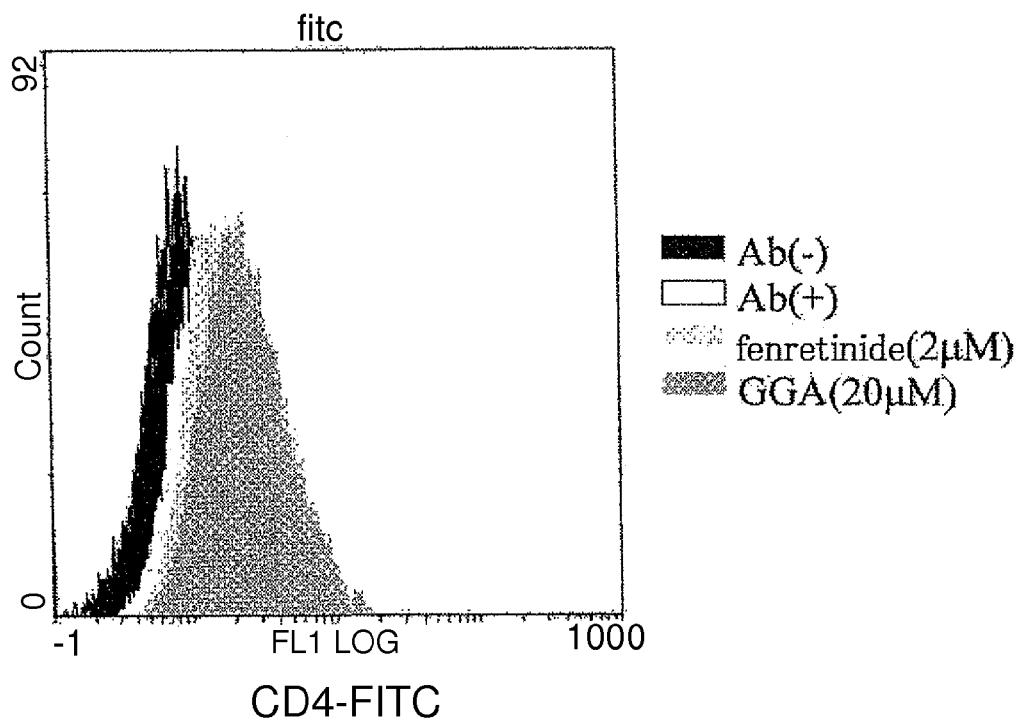
FIG. 7 is a graph showing an influence of fenretinide and GGA on CD4 expression in HeLa/CD4 cells.
Figure 8:
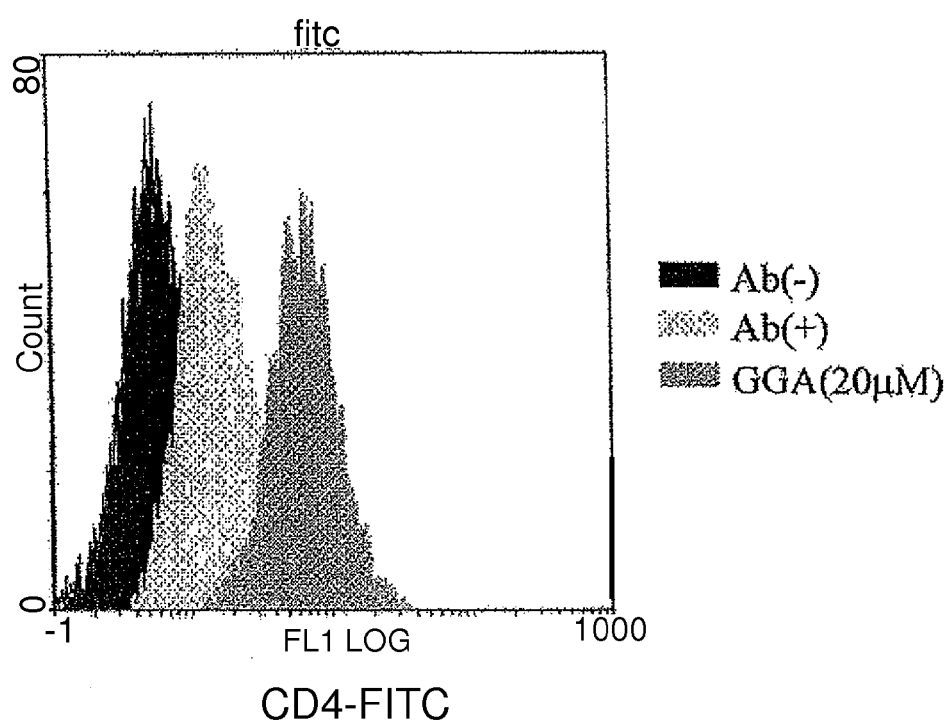
FIG. 8 is a graph showing an influence of GGA on CD4 expression in NP2/CD4/X4 cells.
Figure 9:
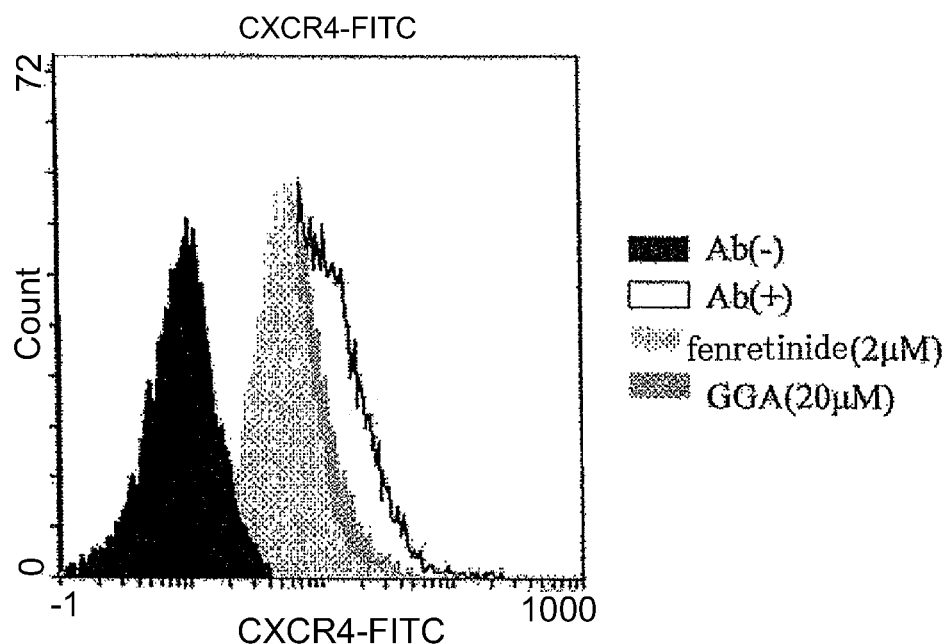
FIG. 9 is a graph showing an influence of fenretinide and GGA on CXCR4 expression in HeLa/CD4 cells.
Figure 10:
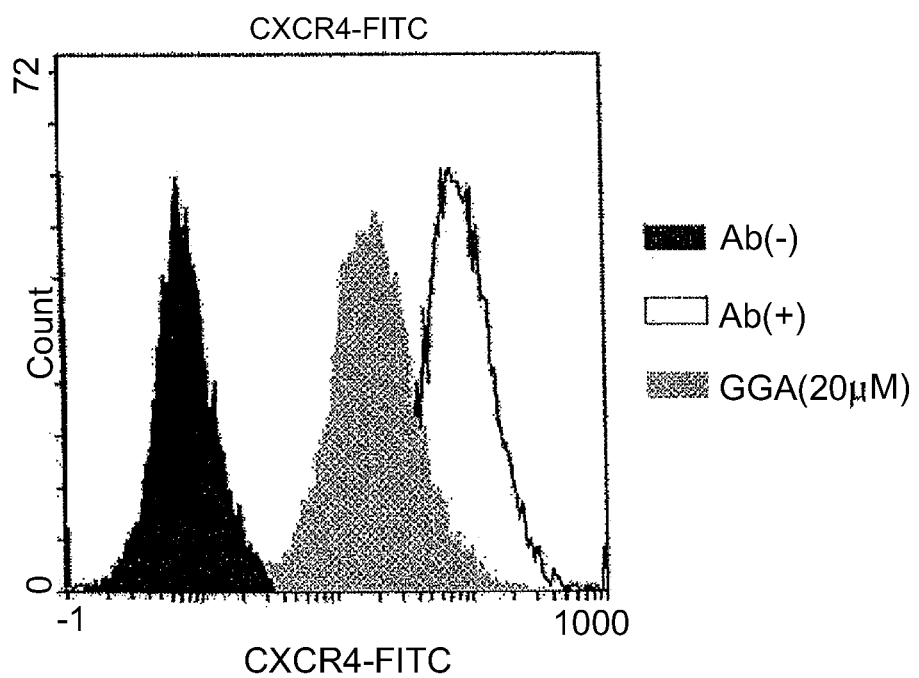
FIG. 10 is a graph showing an influence of GGA on CXCR4 expression in NP2/CD4/X4 cells.

As is clear from Example 1, an HIV vector infection suppressive action was observed in a certain type of retinoid analog. To clarify the mechanism of the infection suppressive action, an influence of retinoid analog on the cell surface expression of CD4 and CXCR4, which are HIV receptors, was analyzed. As a result, both fenretinide and GGA were found to increase CD4 expression in HeLa/CD4 cell and NP2 cell (FIG. 7 and FIG. 8). In contrast, CXCR4 expression was found to decrease by a treatment with fenretinide and GGA (FIG. 9 and FIG. 10).

Conclusion

All fenretinide, GGA and NIK-333 showed an HIV vector infection suppressive effect (anti-HIV activity) and a cell proliferation suppressive effect (cytotoxicity). Fenretinide showed a stronger anti-HIV activity in HeLa/CD4 cell, but weaker than or of the same level as the cytotoxicity in other cells. The anti-HIV activity and cytotoxicity of GGA were of the same level in all cells. In addition, the cytotoxicity of GGA was lower than that of fenretinide. NIK-333 showed a stronger anti-HIV activity than cytotoxicity in all cells. These results reveal that, from among retinoids, NIK-333 particularly has an effective anti-HIV activity.

Example 3

HIV-Infection Suppressive Action and Cell Proliferation Suppressive Action-2

Method

Figure 11:
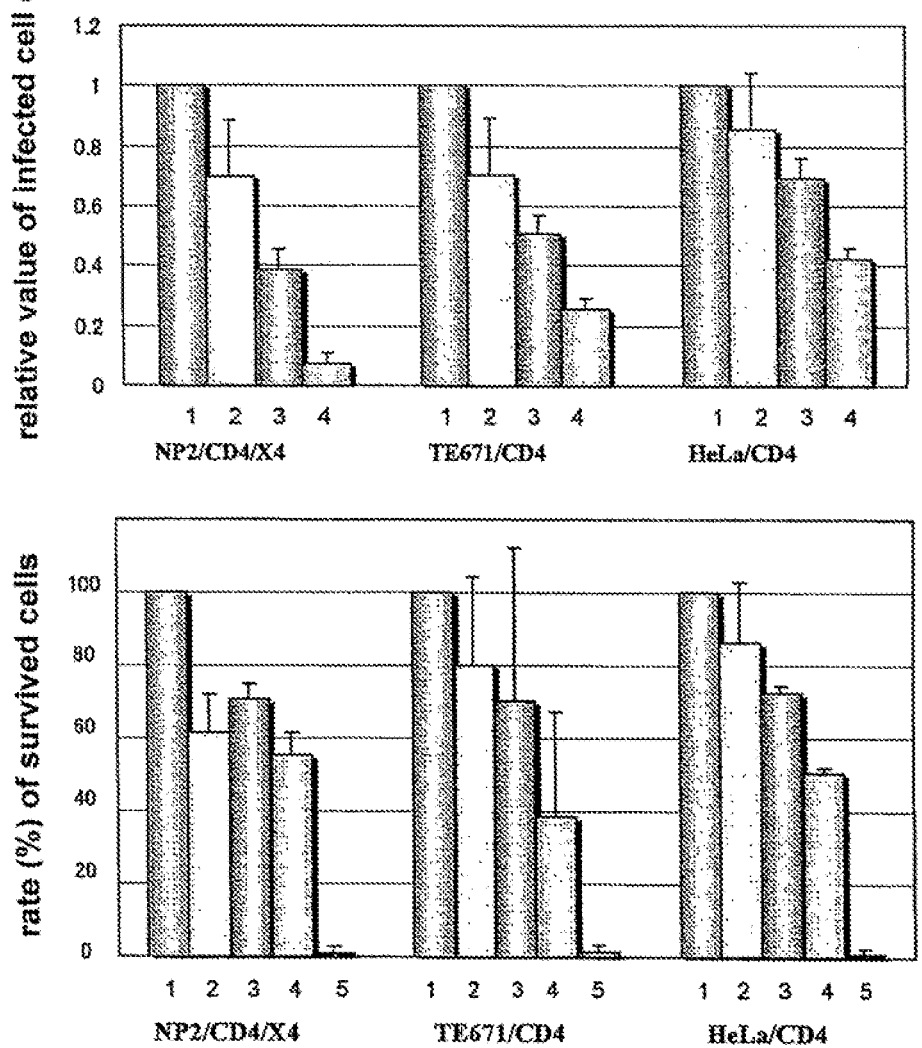
FIG. 11 is a graph showing an influence of GGA on HIV infection and cell proliferation.
Figure 12:
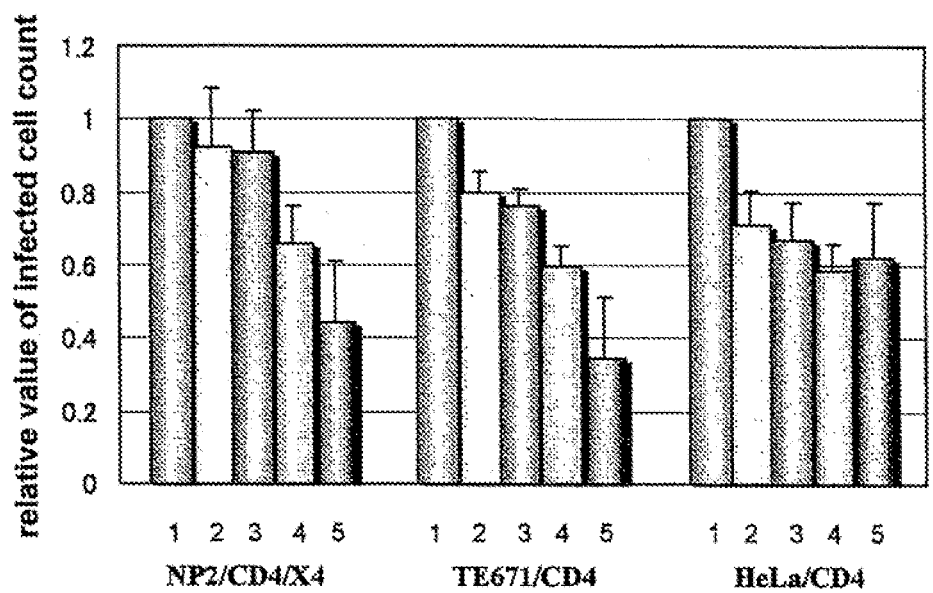
FIG. 12 is a graph showing an influence of fenretinide on HIV infection and cell proliferation.
Figure 12:
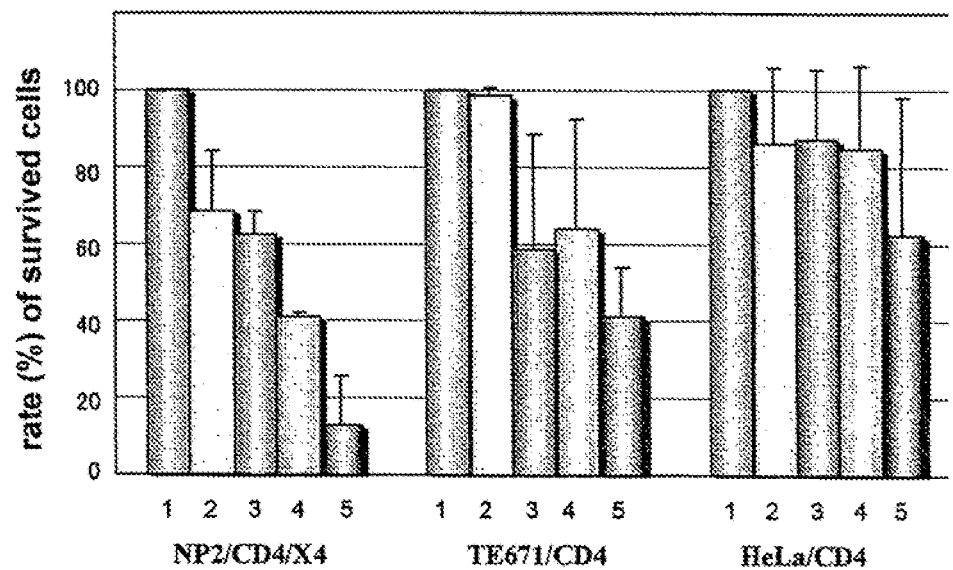
Figure 13:
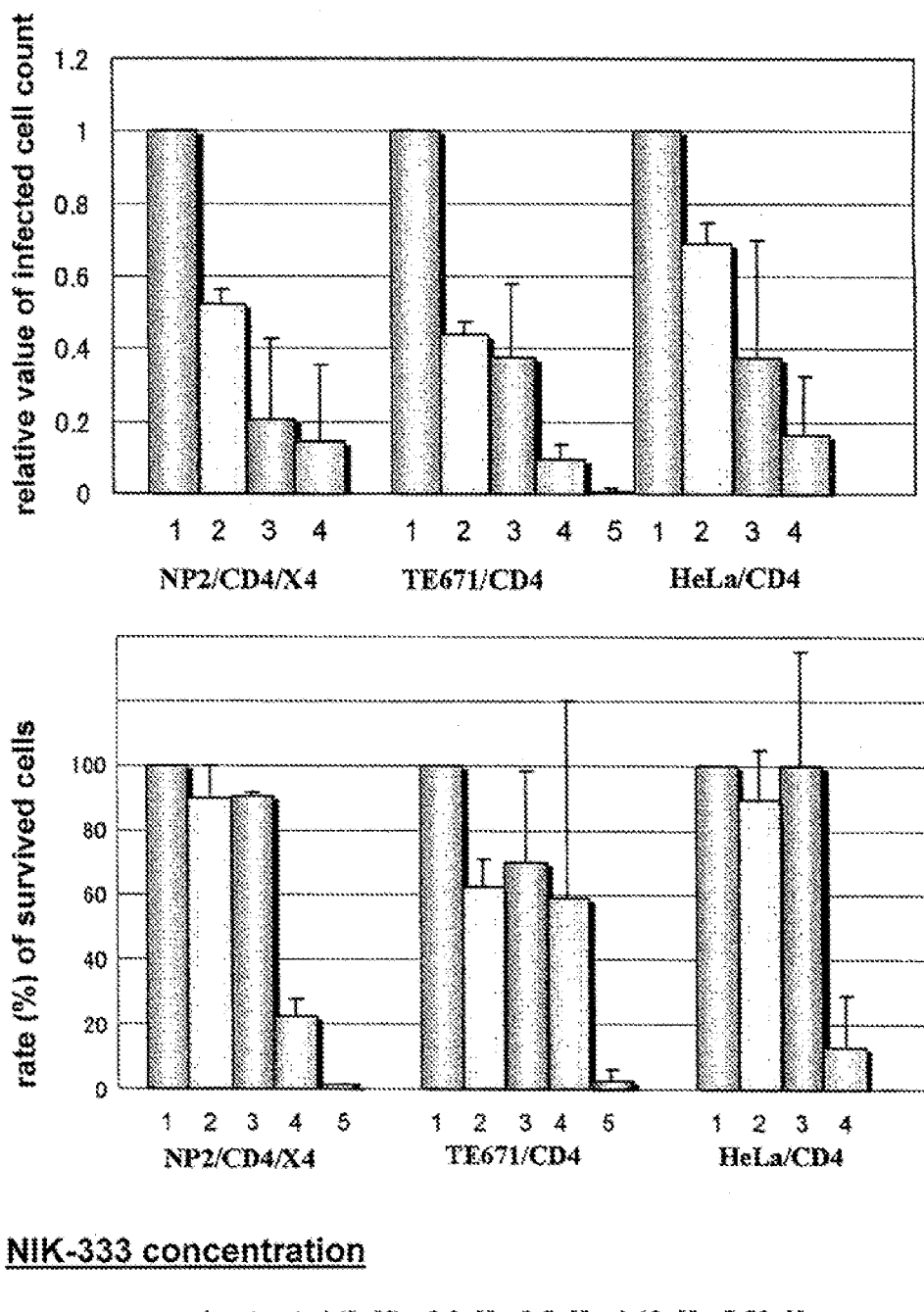
FIG. 13 is a graph showing an influence of NIK-333 on HIV infection and cell proliferation.

In the same manner as in Example 1, the HIV vector infection suppressive action and cell proliferation suppressive action of GGA, fenretinide and NIK-333, which are retinoids, were examined. Examined were NP2/CD4/X4 cell, TE671/CD4 cell and HeLa/CD4 cell. The HIV vector infection suppressive action and cell proliferation suppressive action of GGA are shown in FIG. 11, the HIV vector infection suppressive action and cell proliferation suppressive action of fenretinide are shown in FIG. 12, and the HIV vector infection suppressive action and cell proliferation suppressive action of NIK-333 are shown in FIG. 13.

All retinoids suppressed CXCR4-tropic HXB2 HIV-1 vector infection in a concentration-dependent manner in NP2/CD4/X4 cell, TE671/CD4 cell and HeLa/CD4 cell. These retinoids also suppressed cell proliferation. For example, when NP2/CD4/X4 cell was treated with GGA (20 μM), HIV-1 vector infection was suppressed to 10%, but cell proliferation was only suppressed to 55% (FIG. 11). Similarly, when NP2/CD4/X4 cell was treated with NIK-333 (5 μM), HIV-1 vector-infection decreased to 20%, but cell proliferation was scarcely influenced (FIG. 13). The results reveal that GGA and NIK-333 have a stronger HIV-1 vector-infection suppressive effect than a cell proliferation suppressive effect. In contrast, when NP2/CD4/X4 cell was treated with fenretinide (2 μM), cell proliferation decreased to 10%, but HIV-1 vector-infection was only suppressed to 40%. Fenretinide was shown to have a stronger cell proliferation suppressive effect than an HIV-1 vector-infection suppressive effect. While fenretinide has already been reported to suppress HIV-1 vector infection, it was clarified that GGA and NIK-333 are efficient HIV-1 vector infection inhibitors with less side effects than fenretinide.

Example 4

VSV-Infection Suppressive Action

To clarify whether suppression of HIV vector infection by retinoid is specific to infection via HIV-1 Env protein, the effect of retinoid on infection via vesicular stomatitis virus (VSV)-G protein was observed. VSV is a virus belonging to the genus of Vesiculovirus, Rhabdoviridae, and is enveloped. The genome is a single strand (−)RNA consisting of 11,162 bases.

In the same manner as in Example 1 except using VSV vector instead of HIV vector, VSV infection suppressive action was examined in various cells.

Production of VSV Vector

The following 4 kinds of plasmid DNAs (pLP1, pLP2, pLenti6/V5-GW/LacZ, pLP/VSVG, each 3 μg) were transfected into 293 T cells according to a lipofection method (Mirus or Invitrogen). After 24 hr, the medium was exchanged with a fresh medium. The cells were further cultured for 24 hr, and the culture medium was inoculated to the target cell. The culture medium contains VSV vector.

Figure 14:
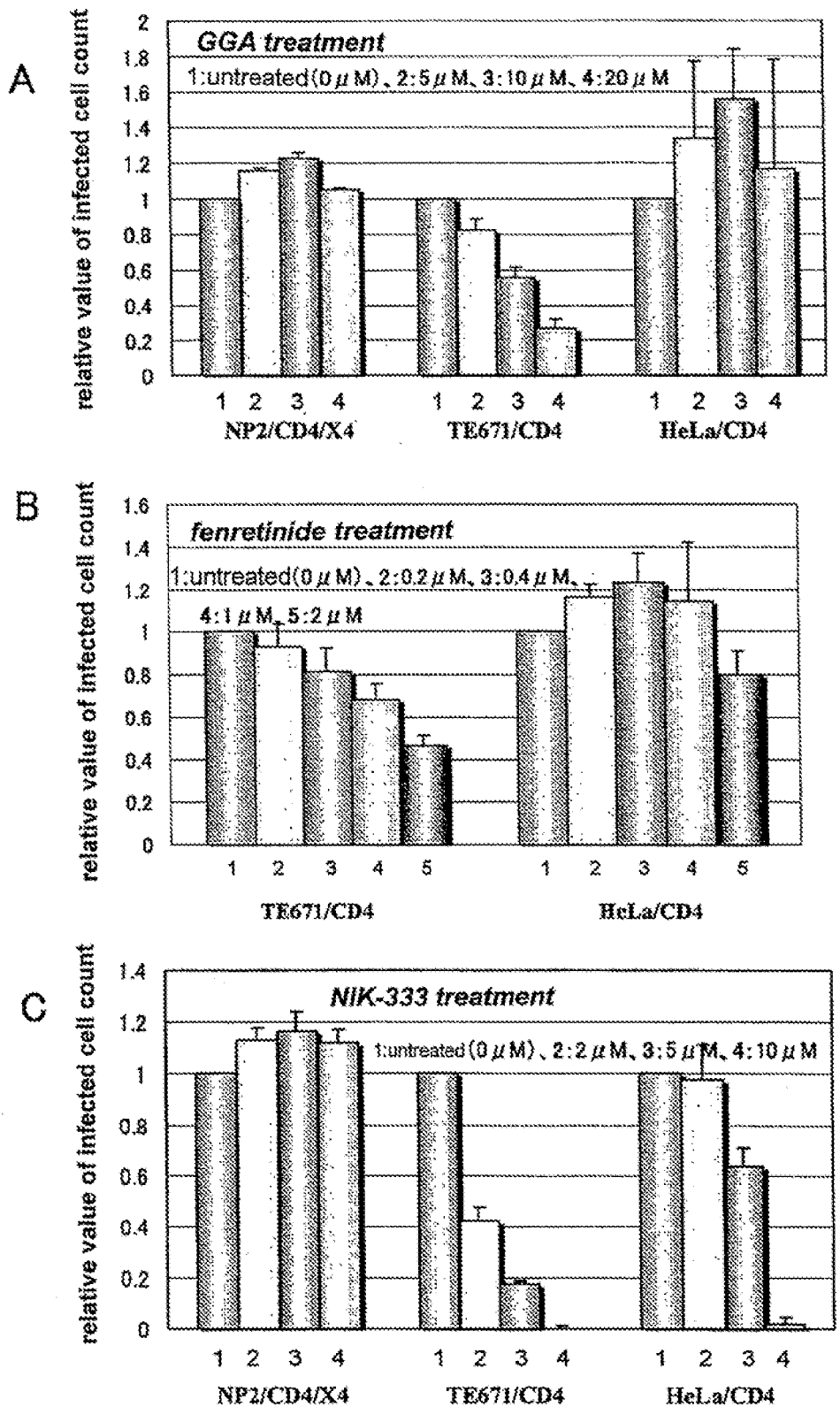
FIG. 14 is a graph showing an influence of retinoid on VSV infection. A:GGA, B:fenretinide, C:NIK-333

As a result, VSV-G protein infection was also suppressed by these retinoids in TE671/CD4 cell (FIG. 14, A-C). The infection with VSV-G protein in NP2/CD4/X4 cell was hardly influenced (FIG. 14, A and C). The infection with VSV-G protein in HeLa/CD4 cell was hardly influenced, either (FIG. 14, A-C). When HeLa/CD4 cell was treated with NIK-333 (10 μM), infection with VSV-G protein was suppressed (FIG. 14, C). However, this result might have been produced by suppression of cell proliferation in the same manner (FIG. 13). These results reveal that retinoid used suppresses infection with HIV-1 Env protein, but does not suppress infection with VSV-G protein in NP2/CD4/X4 cell and HeLa/CD4 cell.

Example 5

Influence of Retinoid on CCR5-Tropic HIV-Infection

In Examples 1-3, the influence of retinoid on CXCR4 tropic HIV-1 vector infection was observed. To know whether retinoid shows a similar influence on CCR5-tropic HIV-1 vector-infection, an influence of JRFL strain, which is CCR5-tropic HIV-1, on Env protein infection was observed.

CCR5 was introduced into TE671/CD4 cell (TE671/CD4/R5 cell) and an experiment was performed in the cell. In the same manner as in Example 1 except CCR5 expression cell was used as the cell to be used and CCR5-tropic HIV-1 was used as a vector, an influence on virus infection was examined.

TE671/CD4/R5 cell was produced as follows. Plasmid DNA encoding neomycin resistance gene and CD4 was transfected into TE671 cell and treated with neomycin. A cell clone expressing CD4 was selected from neomycin resistance cells. This cell was named as TECD4-1. In the same manner as in the production method of TE671/CD4 cell, TECD4-1 cell was infected with mouse leukemia virus vector encoding CCR5, and the cell survived the puromycin treatment was taken as TE671/CD4/R5 cell.

Preparation of CCR5-Tropic HIV Vector pLP1, pLP2, pLenti6/V5-GW/LacZ and JRFL env plasmid DNAs (each 3 μg) were each transfected into 293T cells cultured in a 10 cm culture dish, according to a lipofection method (Mirus or Invitrogen). After 24 hr, the medium was exchanged with a fresh medium. The cells were further cultured for 24 hr, and the culture medium was inoculated to the target cell. The culture medium contains CCR5-tropic HIV vector.

Figure 15:
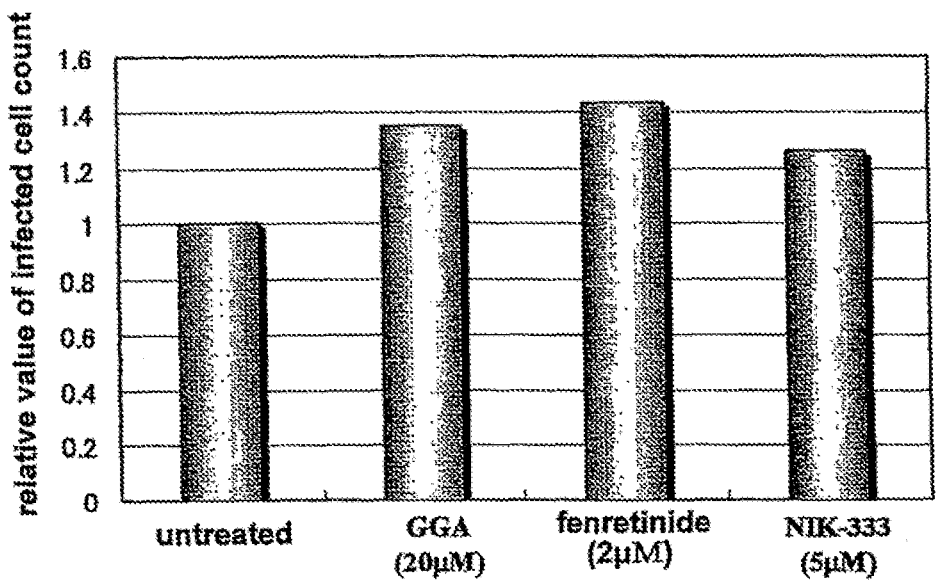
FIG. 15 is a graph showing an influence of retinoid on CCR5-tropic HIV infection.

The results are shown in FIG. 15. Retinoid used was shown to hardly influence infection of a cell, forced to express CCR5, with CCR5-tropic HIV-1 vector (it is often observed that the effect of HIV-1 infection suppressive substance on a cell forced to express infection receptor decreases).

Example 6

Influence of Retinoids on HIV-1 Infection Receptor

HIV-1 enters a cell by membrane fusion of virus membrane and host cell membrane caused by Env protein. Due to the membrane fusion activity of the Env protein, a cell that expresses Env protein causes cell fusion with the host cell to form syncytium. Accordingly, syncytium formation ability of Env protein is considered to reflect intracellular entry of HIV-1. Therefore, intracellular entry of HIV-1 can be quantified by measuring the rate of syncytium formation.

Preparation of Plasmid DNA Used

A DNA fragment containing a LacZ sequence from pLenti6/V5-GW/LacZ plasmid DNA (purchased from Invitrogen) was connected to HIV-1 LTR sequence (provided by Dr. Yokomaku of National Hospital Organization Nagoya Medical Center) and cloned into pBR322 plasmid (purchased from Takara). The plasmid DNA was named as LTR-LacZ.

Quantitative Measurement Method of Syncytium Formation

LTR-LacZ plasmid DNA (3 mg) was transfected into HeLa/CD4 cell and a cell having LTR-LacZ was selected (named as HeLa/CD4/LacZ cell). Since LTR does not initiate transcription in the absence of TAT protein of HIV-1, the cell does not express LacZ. In the same manner as in the infection experiment, HeLa/CD4/LacZ cell was treated with fenretinide, GGA and NIK-333. On the other hand, HXB2 env plasmid DNA (3 mg) was transfected into 293T cells. HXB2 env plasmid DNA simultaneously encodes env and TAT. After 24 hr from transfection, the same number of cells were mixed. 293T cells and HeLa/CD4/LacZ cells are fused by the action of env protein expressed in 293T cells. Then, TAT protein acts on LTR for the first time, transcription is started, and LacZ gene is expressed. The LacZ activity was quantified using a high sensitive beta-galactosidase assay kit (purchased from Stratagene), and the value thereof was taken as syncytium formation efficiency.

Figure 16:
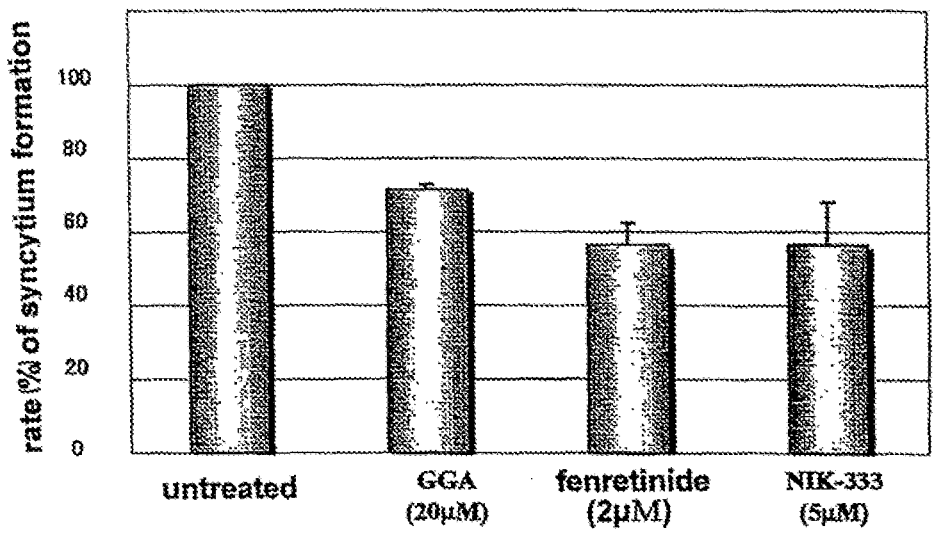
FIG. 16 is a graph showing an influence of retinoid on syncytium formation.

The results reveal that these retinoids suppress cell fusion by HIV-1 Env protein (FIG. 16). In other words, suppression of HIV-1 vector infection by retinoids used is suggested to be attributable to the inhibition of the HIV-1 intracellular entry process.

To know whether suppression of HIV-1 vector infection by these retinoids is attributable to an influence on the expression of CD4 and CXCR4, which are HIV-1 infection receptors, expression of CD4 and CXCR4 was analyzed by FACS. Concrete processes are similar to those in Example 2. Black region shows data in the absence of an antibody and white region shows data in the presence of an antibody.

Figure 17:
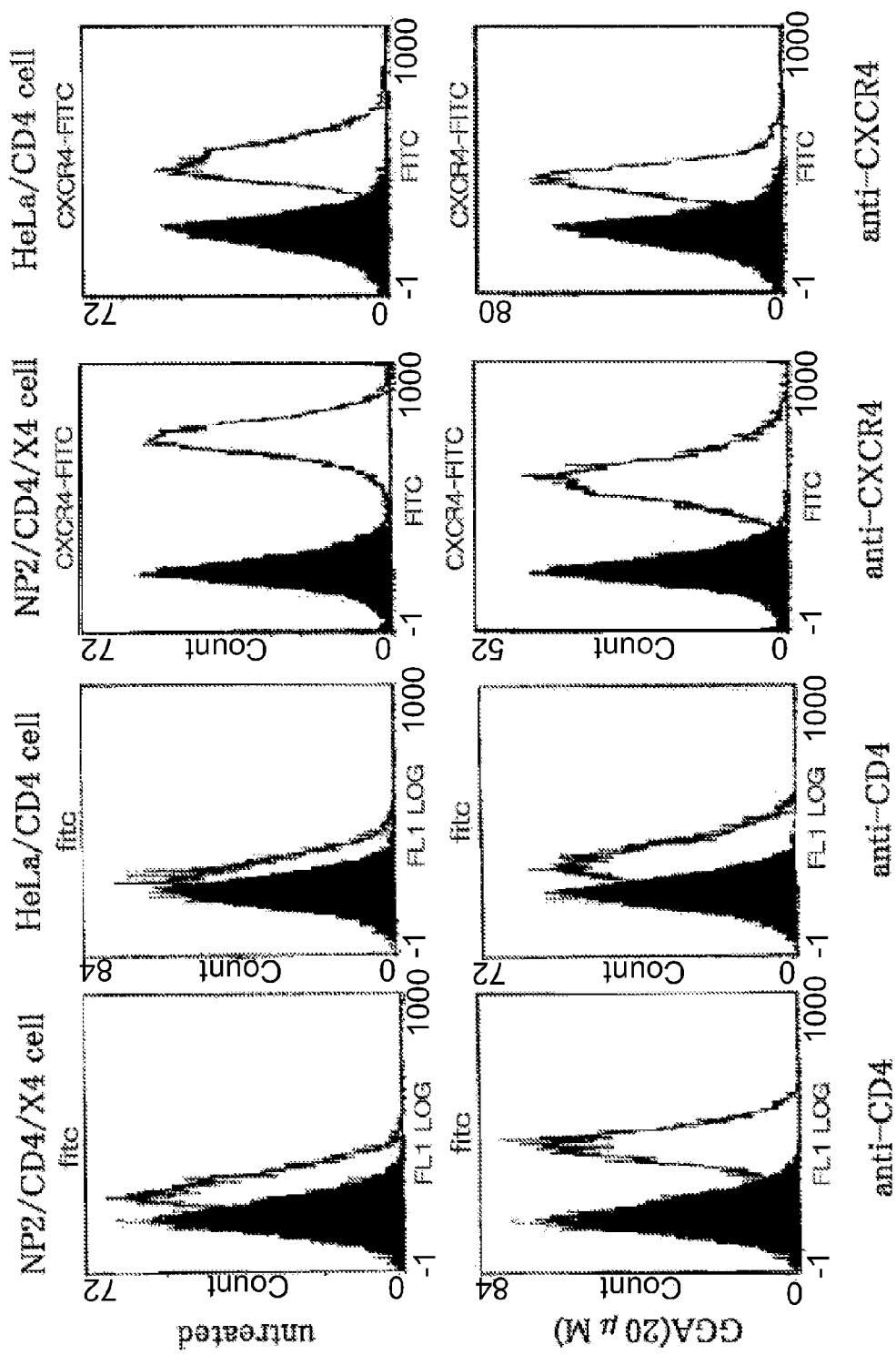
FIG. 17 is a graph showing an influence of GGA on CD4 cell surface expression and CXCR4 cell surface expression.
Figure 18:
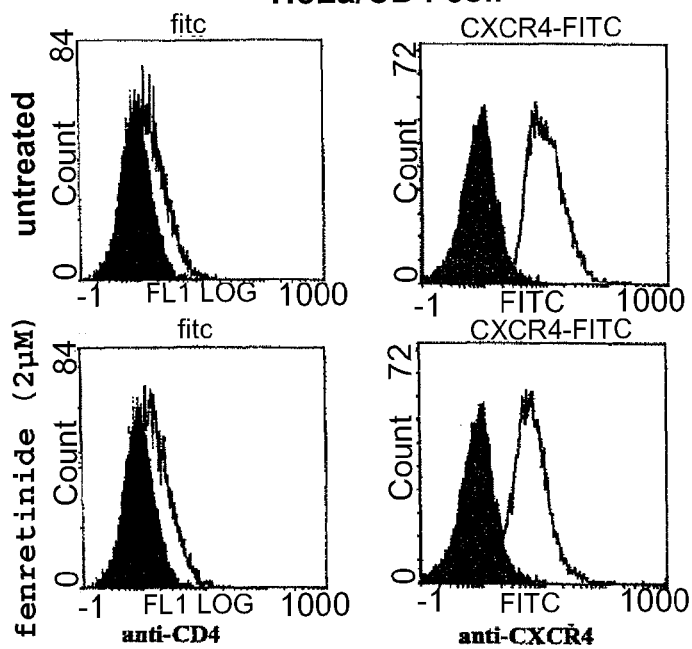
FIG. 18 is a graph showing an influence of fenretinide on CD4 cell surface expression and CXCR4 cell surface expression.
Figure 19:
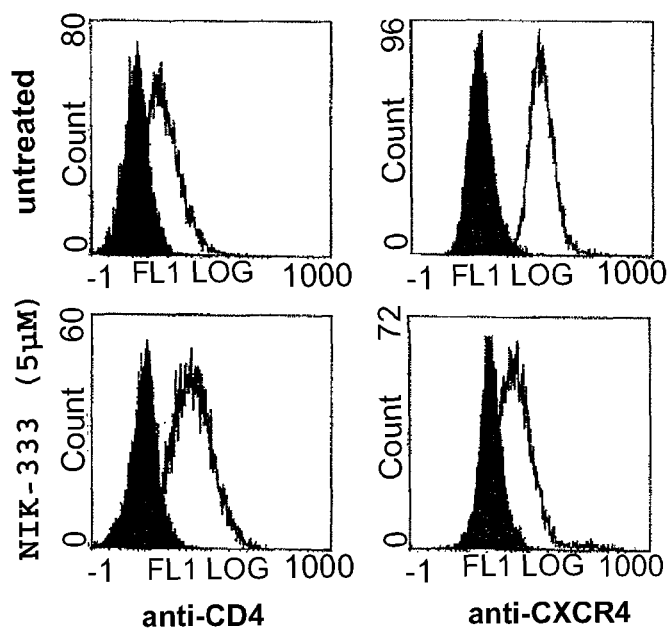
FIG. 19 is a graph showing an influence of NIK-333 on CD4 cell surface expression and CXCR4 cell surface expression.

The results reveal that GGA (FIG. 17), fenretinide (FIG. 18) and NIK-333 (FIG. 19) tend to increase cell surface expression of CD4 and decrease cell surface expression of CXCR4.

This application is based on application No. 2006-312040 filed in Japan, the contents of which are incorporated hereinto by reference.

The invention claimed is:

1. A method of suppressing an early stage of retrovirus infection, comprising administering an effective amount of an inhibitor of a retrovirus infection, wherein the inhibitor comprises, as an active ingredient, at least one compound selected from the group consisting of a compound represented by formula (I), a salt of a compound represented by formula (I), a compound represented by formula (II), and a salt of a compound represented by formula (II):

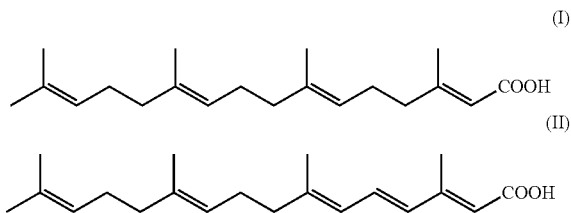

to a subject in need thereof,
wherein the retrovirus infection is a human immunodeficiency virus (HIV) infection.

2. The method of claim 1, wherein the suppression of an early stage of retrovirus infection is based on a CXCR4 expression lowering action.

3. The method of claim 1, wherein the suppression of an early stage of retrovirus infection is specific to suppression of infection via human immunodeficiency virus-1 (HIV-1) Env protein.

4. The method of claim 1, wherein the suppression of an early stage of retrovirus infection is based on inhibition of intracellular entry of HIV.

* * * * *